United States Patent [19]

Devries et al.

[11] Patent Number: 4,814,533

[45] Date of Patent: Mar. 21, 1989

[54] ENHANCING THE PRODUCTION OF AROMATICS IN HIGH TEMPERATURE, HIGH SPACE VELOCITY CATALYTIC CONVERSION OF LOWER MOLECULAR WEIGHT HYDROCARBONS TO HIGHER MOLECULAR WEIGHT HYDROCARBONS

[75] Inventors: Loius Devries, Greenbrae; P. R. Ryason, Santa Rosa, both of Calif.

[73] Assignee: Chevron Research Company, San Francisco, Calif.

[21] Appl. No.: 794,215

[22] Filed: Oct. 31, 1985

[51] Int. Cl.$^4$ .......................................... C07C 15/393
[52] U.S. Cl. .................................... 585/407; 585/415; 585/417; 585/500; 585/654; 585/656; 585/700; 585/943
[58] Field of Search ............... 585/500, 407, 415, 417, 585/654, 656, 700, 943

[56] References Cited

U.S. PATENT DOCUMENTS 4,507,517  3/1985  DeVries et al. ...................... 585/415
4,547,610  10/1985  Sofranko et al. ................... 585/500

OTHER PUBLICATIONS

Hackh's Chemical Dictionary, 4th Ed., p. 448.

Primary Examiner—William R. Dixon, Jr.
Assistant Examiner—Ellen McAvoy
Attorney, Agent, or Firm—S. R. La Paglia; R. C. Gaffney; J. J. DeYoung

[57] ABSTRACT

In a continuous catalytic process for the production of higher molecular weight hydrocarbons from lower molecular weight hydrocarbons in which a lower molecular weight hydrocarbon containing gas is contacted in a reaction zone with a higher molecular weight hydrocarbon synthesis catalyst under $C_2+$ hydrocarbon synthesis conditions, the improvement comprising adding hydrogen to said gas thereby forming a reaction gas wherein said hydrogen comprises 1 to 25 volume percent of the reaction gas, said synthesis conditions including a temperature greater than 1000° C. and a gas hourly space velocity of greater than 3200 hr$^{-1}$.

25 Claims, No Drawings

ENHANCING THE PRODUCTION OF AROMATICS IN HIGH TEMPERATURE, HIGH SPACE VELOCITY CATALYTIC CONVERSION OF LOWER MOLECULAR WEIGHT HYDROCARBONS TO HIGHER MOLECULAR WEIGHT HYDROCARBONS

FIELD OF THE INVENTION

The present invention relates to a catalytic process for the production of higher molecular weight hydrocarbons from lower molecular weight hydrocarbons. More particularly, the present invention is concerned with the production of aromatic hydrocarbons in a catalytic methane conversion process.

BACKGROUND OF THE INVENTION

It is the business of many refineries and chemical plants to obtain, process and upgrade relatively low value hydrocarbons to more valuable feeds, or chemical raw materials. For example, methane, the simplest of the saturated hydrocarbons, is often available in rather large quantities either as an undesirable by product in admixture with other more valuable higher molecular weight hydrocarbons, or as a component of an off gas from a process unit, or units. Though methane is useful in some chemical reactions, e.g., as a reactant in the commercial production of methanol and formaldehyde, it is not as useful a chemical raw material as most of the higher molecular weight hydrocarbons. For this reason process streams which contain methane are usually burned as fuel.

Methane is also the principal component of natural gas, which is composed of an admixture of normally gaseous hydrocarbons ranging $C_4$ and lighter and consists principally of methane admixed with ethane, propane, butane and other saturated, and some unsaturated hydrocarbons. Natural gas is produced in considerable quantities in oil and gas fields, often at remote locations and in difficult terrains, e.g., offshore sites, arctic sites, swamps, deserts and the like. Under such circumstances the natural gas is often flared while the oil is recovered, or the gas is shut in, if the field is too remote for the gas to be recovered on a commercial basis. The construction of pipelines to carry the gas is often not economical, due particularly to the costs of connecting numerous well sites with a main line. Transport of natural gas under such circumstances is also uneconomical because methane at atmospheric pressure boils at $-258°$ F. and transportation economics dictate that the gas be liquefiable at substantially atmospheric pressures to reduce its volume. Even though natural gas contains components higher boiling than methane, and such mixtures. can be liquefied at somewhat higher temperatures than pure methane, the temperatures required for condensation of the admixture is nonetheless too low for natural gas to be liquefied and shipped economically. Under these circumstances the natural gas, or methane, is not even of sufficient value for use as fuel, and it is wasted.

The thought of utilizing methane from these sources, particularly avoiding the tremendous and absolute waste of a natural resource in this manner, has challenged many minds, but has produced few solutions. It is highly desirable to convert methane to hydrocarbons of higher molecular weight (hereinafter, $C_2+$) than methane, particularly admixtures of $C_2+$ hydrocarbon products which can be economically liquefied at remote sites; especially admixtures of $C_2+$ hydrocarbons rich in ethylene or benzene, or both. Ethylene and benzene are known to be particularly valuable chemical raw materials for use in the petroleum, petrochemical, pharmaceutical, plastics and heavy chemicals industries. Ethylene is thus useful for the production of ethyl and ethylene compounds including ethyl alcohol, ethyl ethers, ethylbenzene, styrene, polyethylbenzenes ethylene oxide, ethylene dichloride, ethylene dibromide, acetic acid, oligomers and polymers and the like. Benzene is useful in the production of ethylbenzene, styrene, and numerous other alkyl aromatics which are suitable as chemical and pharmaceutical intermediates, or suitable in themselves as end products, e.g., as solvents or high octane gasoline components.

It has been long known that methane, and natural gas can be pyrolytically converted to $C_2+$ hydrocarbons. For example, methane or natural gas passed through a porcelain tube at moderate red heat will produce ethylene and its more condensed homologs such as propylene, as well as small amounts of acetylene and ethane. Methane and natural gas have also been pyrolytically converted to benzene, the benzene usually appearing in measurable quantities at temperatures above about 1650° F. (899° C.), and perhaps in quantities as high as 6–10 wt. % at 2200° F. to 2375° F., (1204° to 1302° C.) or higher. Acetylene and benzene in admixture with other hydrocarbons, have been produced from methane and natural gas in arc processes, cracking processes, or partial combustion processes at temperatures ranging above about 2775° F. (1524° C.). Heat for such reactions has been supplied from various sources including electrically heated tubes, electric resistance elements, and spark or arc electric discharges. These processes characteristically require considerable heat energy which, most often, is obtained from combustion of the by-product gases. The extreme temperatures coupled with the low yields of higher molecular weight hydrocarbons such as benzene an other aromatics have made the operation of such pyrolytic processes uneconomical.

High temperature, noncatalytic, thermal pyrolysis processes involving the conversion of methane in the presence of ethane and other hydrocarbons are well known in the art. Representative articles include: Roczniki Chemi, An. Soc. Chim. Polonorum, 51, 1183 (1977), "The Influence of Ethane on Thermal Decomposition of Methane Studied By The Radio Chromatographic Pulse Technique"; J. Soc. Chem. Ind. (Trans. and Comm.) 1939,58, 323-7; and J. Chin. Chem. Soc. (Taipei) 1983, 30(3), 179-83.

Addition of hydrogen to pyrolysis reaction mixtures is well known, see for example, pp 84–85 in "Pyrolysis Theory and Industrial Practice", L. F. Albright, B. L. Crynes and W. H. Corcoran (Ed.), Academic Press (1983).

Partial oxidation processes of converting methane to $C_2+$ hydrocarbons are well known. In these processes, hydrogen must be removed either as water, molecular hydrogen or other hydrogen-containing species. Likewise, any other polymerization mechanism wherein methane is converted to $C_2+$ hydrocarbon products requires a tremendous amount of energy, most often supplied as heat, to provide the driving force for the reactions. In the past the molecular hydrogen liberated by the reaction has often been separated and burned to provide the necessary process heat. This route has proven an abomination to the production of $C_2+$ hydrocarbons, but alternate reaction pathways have appeared little better, if any, for these have resulted in the production of large quantities of the higher, less useful hydrogen deficient polymeric materials such as coke, and highly oxidized products such as carbon dioxide and water.

Typical of low temperature prior art oxidation processes are those disclosed in U.S. Pat. Nos. 4,239,658, 4,205,194 and 4,172,180 which use a regenerable catalyst-reagent U.S Pat. No. 4,239,658, for example, teaches a process for the conversion of methane to higher molecular weight hydrocarbons. In the process, a three component catalyst-reagent is utilized which comprises a mixture of various metals and metal oxides, particularly a Group VIII noble metal, nickel or a Group VI-B noble metal, a Group VI-B metal oxide and a Group II-A metal. The patent teaches process temperatures from about 1150° to 1600° F. (621° to 871° C.), preferably 1250° F. to about 1350° F. (677° to 732° C.).

It has also been reported in Science 153, 1393, (1966), "High Temperature Synthesis of Aromatic Hydrocarbons From Methane", that aromatic hydrocarbons can be prepared from methane by contact with silica at 1000° C. (1832° F.). The yield of hydrocarbons was in the range of 4.8 to 7.2 percent based on the methane used in a single pass at a space velocity of 1224 $hr^{-1}$.

In the J. Chinese Chem. Soc., Volume 29, pages 263-273 (1981), it is reported that methane can be converted to $C_2+$ hydrocarbons at temperatures of 800° to 1130° C. and space velocities of 3100 $hr^{-1}$ or less using a metal oxide catalyst. However, the total conversion of methane, at best, is 7.5 mole percent using a thorium oxide catalyst.

Franz Fischer, reports in an article entitled: "The Synthesis of Benzol Hydrocarbons From Methane At Ordinary Pressure and Without Catalyst" (Brennstoff-Chemie, Vol. 9, pp. 309-316, 1928) that methane is converted to benzol hydrocarbons by passing methane through a hot tube. In carrying out this work Fischer tested many substances for catalytic activity at temperatures ranging from 650° to 1150° C. and at high flow rates and concluded that the substances tested were not catalytic and not necessary. Among the substances tested were elemental iron, copper, tungsten, molybdenum, tin and carbon; and the compounds potassium hydroxide and silica gel.

SUMMARY OF THE INVENTION

In a continuous catalytic process for the production of higher molecular weight hydrocarbons from lower molecular weight hydrocarbons in which a lower molecular weight hydrocarbon containing gas is contacted in a reaction zone with a higher molecular weight hydrocarbon synthesis catalyst under $C_2+$ hydrocarbon synthesis conditions, the improvement comprising adding hydrogen to said gas thereby forming a reaction gas wherein said hydrogen comprises 1 to 25 volume percent of the reaction gas, said synthesis conditions including a temperature greater than 1000° C. and a gas hourly space velocity of greater than 3200 $hr^{-1}$.

DETAILED DESCRIPTION OF THE INVENTION

It has been found in the present invention that in the catalytic conversion of lower molecular weight hydrocarbons to higher molecular weight hydrocarbons that the yield of higher molecular weight hydrocarbons, particularly the light aromatics, are dramatically increased by the addition of a small amount of hydrogen to the feed gas.

As used in the present invention the phrase "lower molecular weight hydrocarbons" means hydrocarbons containing at least one or more carbon atoms, i.e., methane, ethane, propane, etc. Also as used in the present invention, the phrase "higher molecular weight hydrocarbons" means hydrocarbons containing two or more carbon atoms and at least one carbon atom more than the lower molecular weight hydrocarbon in the feedstock.

As used herein the phrase "$C_2+$ hydrocarbon synthesis conditions" refers to the selection of feedstock, reaction temperature, space velocity and catalyst described hereafter such that higher molecular weight hydrocarbons are produced in the process with yields as described hereafter. Other process parameters necessary to maintain $C_2+$ hydrocarbon synthesis conditions, such as the selection of particular types of reaction vessels, etc., is readily determined by any person skilled in the art.

As used in the present invention the word "metal" refers to all those elements of the periodic table which are not non-metals. "Non-metals" for the purpose of the present invention refers to those elements having atomic numbers 1, 2, 5 through 10, 14 through 18, 33 through 36, 52 through 54, 85 and 86.

The word "catalyst" is used in the present invention to mean a substance which strongly affects the rate of a chemical reaction but which itself undergoes no chemical change although it may be altered physically by chemically absorbed molecules of the reactants and reaction products.

As used in the present invention the phrase "continuous catalytic process" means a process in which feedstock and products are simultaneously fed to and removed from a reaction zone containing a catalyst.

As used in the present invention the phrase "reaction gas" refers to the gas or gas mixture being fed to the catalyst-containing reaction zone.

As used in the present invention the words "light aromatics" refers to single ring aromatic hydrocarbons, for example, benzene, toluene, xylenes, and so forth.

The Reaction Gas and Products

The reaction gas of the present invention will comprise lower molecular weight hydrocarbons and sufficient added hydrogen to significantly increase the yield of light aromatic hydrocarbons. The lower molecular weight hydrocarbon will comprise methane or natural gas containing $C_1$ to $C_4$ hydrocarbons.

Generally enough hydrogen is added to increase the the yield of light aromatic hydrocarbons by 10 to 40 weight percent as compared to a reaction gas consisting of 100% methane. Generally, the hydrogen is added so that the reaction gas comprises 1 to 25 volume percent added hydrogen. Preferably, the added hydrogen content in the reaction gas comprises 2 to 20 volume percent and more preferably 5 to 15 volume percent.

The reaction gas can also contain other nonhydrocarbon gases such as nitrogen and carbon dioxide.

The product higher molecular weight hydrocarbons will comprise $C_2+$ hydrocarbons, particularly mixtures of $C_2+$ hydrocarbons which can be economically liquefied. Preferably, the higher molecular weight hydrocarbon product streams will be rich in ethylene or aromatics such as benzene, or both. The product stream will also contain copious amounts of hydrogen. The hydrogen added to the reaction gas can of course be obtained from the product gas.

The process of the present invention affords high conversions of the lower molecular weight hydrocarbons with high selectivity to higher molecular weight hydrocarbons. More particularly, as measured by the disappearance of the lower molecular weight hydrocarbons, the process of the present invention affords conversions of 19 mole percent or more of the lower molecular weight hydrocarbons, and preferably, the conversions are greater than 25 mole percent and more preferably greater than 40 mole percent. The carbon-containing reaction products comprise 80 mole percent or more of higher molecular weight hydrocarbons, preferably, greater than 90 mole percent. Based on the feed, at least 15 mole percent, and preferably at least 20 mole percent, and more preferably at least 40 mole percent of the lower molecular weight hydrocarbons is converted to higher molecular weight hydrocarbons which is referred to herein as selectivity.

Process Conditions

It is essential to the process of the present invention that a high temperature greater than 1000° C. is maintained in the reaction zone along with a high gas hourly space velocity of greater than 3200 $hr^{-1}$. Preferably, the temperature will be greater than 1100° C. with a space velocity greater than 6000 $hr^{-1}$. Still more preferably the temperature is greater than 1150° C. with a space velocity greater than 9000 $hr^{-1}$.

Generally, the temperature will be in the range of 1001° to 1300° C. while the gas hourly space velocity is in the range 3200 to 360,000 $hr^{-1}$. Preferably, the temperature is in the range 1100° to 1200° C. with a gas hourly space velocity of 6,000 to 36,000 $hr^{-1}$. More preferably the temperature is in the range 1150° to 1175° C. with a gas hourly space velocity in the range of 9,000 to 18,000 $hr^{-1}$. Generally, high temperatures are used with high space velocities and low temperatures are used with low space velocities.

The process can be operated at sub-atmospheric, atmospheric, or supra atmospheric pressure to react and form the higher molecular weight $C_2+$ hydrocarbons. It is preferred to operate at atmospheric pressure or within about 15 psi of atmospheric pressure.

The Catalysts

The lower molecular weight hydrocarbons is introduced into a reaction zone containing a suitable hydrocarbon synthesis catalyst. The reaction-zone catalyst system can be either of the fixed bed type or fluid bed type and the lower molecular weight hydrocarbons can be introduced into the top or bottom of the reaction zone with the product stream removed from either the top or bottom. Preferably, a fixed bed catalyst system is used and the feed stream is introduced into the top of the reaction zone and product is withdrawn from the bottom.

A wide range of catalysts can be used in the present invention. Many commercially available catalysts which have been used in different processes are suitable for use in the process of the present invention. The word "catalyst" is used in the present invention to mean a substance which strongly affects the rate of a chemical reaction but which itself undergoes no chemical change although it may be altered physically by chemically absorbed molecules of the reactants and reaction products. It is also understood that the catalyst of the present invention may be formed in situ. For example, in the present invention when an oxide, nitride, or carbide metal catalyst is initially charged to the reactor, the oxide and nitride may be converted in situ to the carbide which then functions as the catalytic species.

Catalysts useful in the present invention may be used with and without catalyst supports. However, it is generally preferred to use a catalyst support such as the well known aluminas.

The catalysts useful in the present invention may have a wide range of surface areas as measured by the BET method using krypton [Jour. Am. Chem. Soc., vol. 60, pp 309 (1938)]. Low surface areas are preferred. Generally, the catalyst will have a surface area in the range 0.1 to 10 $m^2$/gram, preferably in the range 0.2 to 2.0 $m^2$/gram.

The hydrocarbon synthesis catalysts useful in the present invention will provide conversion of at least 19% of the lower molecular weight hydrocarbons and will maintain this conversion for at least 3 hours under the temperature and space velocity conditions previously discussed. Preferred catalysts of the present invention will provide conversions of 30% or more of the lower molecular weight hydrocarbons feed and remain active for 3 hours or more.

Particularly preferred catalysts are those described in our copending application entitled "Conversion of Low Molecular Weight Hydrocarbons to Higher Molecular Weight Hydrocarbons Using a Metal-containing Catalyst", Ser. No. 547,699, filed Oct. 31, 1983, the entire disclosure of which is incorporated herein by reference. A useful silicon-containing catalyst is disclosed in our copending application entitled: "Conversions of Low Molecular Weight Hydrocarbons to Higher Molecular Weight Hydrocarbons Using a Silicon Compound-Containing Catalyst", Ser. No. 547,697, filed Oct. 31, 1983, the disclosure of which is incorporated herein by reference. A useful boron compound containing catalyt is described in U.S. Pat. No. 4,507,517, the disclosure of which is incorporated herein by reference.

The hydrocarbon synthesis catalysts useful in the present invention may be a metal compound-containing catalyst or non-metal compound-containing catalyst or mixtures thereof.

Metal-Compound Containing Catalysts

A wide range of metal compound-containing catalysts and catalyst supports may be used in the present invention.

Representative metal compound-containing catalysts are refractory materials and include the compounds of the Group I-A, II-A, III-A, IV-B or actinide series metals. Representative compounds include the carbide, nitride, boride or oxide of a Group I-A, II-A, III-A, IV-B or actinide series metal, used alone or in combination.

The catalyst must be thermally stable under the operating condition in the reaction zones and are preferably particulate in form. The carbides of the Groups I-A, II-A, III-A, IV-B and actinide series metals are particularly preferred because it is believed that the carbide metal compound-containing catalyst are the most stable under the severe reaction conditions of the present invention. Preferably, the catalyst can also be regenerated by the periodic burning-off of any undesirable deposits such as coke. The regeneration of catalyst by the burning off coke is well known in the catalyst and petroleum processing art.

Representative Group I-A metal compound-containing catalyst include the carbide, nitride, boride, oxide of lithium, sodium, potassium, rubidium, and cesium. Most preferred among the Group I-A metals is lithium.

Representative Group II-A metal compound-containing catalysts include the carbide, nitride, boride, or oxide of beryllium, magnesium, calcium, strontium, barium, and radium. Most preferred among the Group II-A metals is calcium.

Representative Group III-A metal compound-containing catalysts include the carbide, nitride, boride, or oxide of aluminum, scandium, yttrium, lanthanum, and actinium. Most preferred among the Group III-A metals is aluminum.

Representative Group IV-B metal compound-containing catalysts include the carbide, nitride, boride, or oxide of titanium, zirconium, hafnium, and zirconium. Most preferred among the Group IV-B metals is zirconium. Representative actinide series metal compound-containing catalysts include the carbide, nitride, boride, or oxide of thorium and uranium. Most preferred among the actinide series metals is thorium.

A particularly preferred catalyst for use in the present invention is thorium oxide on alumina.

Non-Metal Compound Containing Catalysts

Representative non-metal compound containing catalysts are catalysts containing compounds of boron and silicon.

Representative boron compound containing catalysts are refractory materials and include boron carbide, or boron nitride. Particularly preferred is boron nitride.

Representative silicon compound-containing catalysts are refractory materials and include silicon carbide, nitride, silicon boride or silicon oxide. Particularly preferred is silicon carbide.

The advantages of the present invention will be readily apparent from a consideration of the following examples.

The examples illustrating the invention were carried out as follows:

The apparatus comprises a vertical reactor tube made of high purity alumina of ⅜" O.D. and ¼" I.D. This tube is 24" long, the central 12" of which is surrounded by a high temperature electric furnace (Marshall Model 1134). The heated section of the tube is packed with the test catalyst. A small piece of close fitting alumina honeycomb, or monolith, at the bottom of the bed supports the catalyst. An "O"-ring sealed closure at the top of the reactor tube connects it to a gas flow system, which permits either argon or methane to be passed into the reactor at a measured rate. Gas flows into the reactor are measured with pre-calibrated flowmeters. Gas exiting from the reactor is first passed through a trap packed with dry stainless steel "saddles" (distillation column packing), then through a tube fitted with a rubber septum. Gas samples are taken through the septum with a syringe. Off gas exits the system through a "U"-tube partially filled with oil. Bubbles passing through the oil provide a visual indicator of the gas flow.

In operation, the central section of the reactor tube is packed with the catalyst to be tested. The catalyst particles range in size from 8 mesh to 12 mesh. About 10 cm$^3$ of catalyst is charged to the reactor. The reactor is then placed in the cold furnace, and the necessary input and output connections are made. A slow flow of about 15 to 20 ml/min. of argon is continuously passed through the reactor, which is then brought to the desired temperature over a period of about 150 min. Temperatures. reported herein are measured in the furnace wall. Temperatures are measured by a thermocouple mounted in the furnace wall. Calibration curves, previously developed from a thermocouple in the catalyst bed and compared to the furnace wall thermocouple, are used to determine the reaction temperatures reported herein.

Once the apparatus is at the desired temperature, argon flow is stopped and methane flow is started at the predetermined flow rate. Space velocities are calculated on the basis of the temperature, pressure, methane flow rate into the reactor and on the catalyst bed dimensions. On each run, the reaction is allowed to level out for 15 to 20 minutes before the first analytic sample is withdrawn through the septum. Two samples are taken each time, using one ml gas-tight syringes. Aliquots of these samples (0.25 ml) are separately injected into a gas chromatograph packed with Poropak Q. Analysis is made for hydrogen, methane, and light hydrocarbons having less than 5 atoms of carbon. Other aliquots of the same samples are injected into another gas chromatograph column packed with Bentone 1200. This analysis is made for aromatics, including benzene, toluene, xylenes, etc.

EXAMPLES

The Tables below illustrate the effect of adding hydrogen to the reaction feed gas in the conversion of methane.

TABLE I

Constant Conversion of 18%, GHSV = 9000 hr$^{-1}$

| Temperature, °C. | % H$_2$ (Balance CH$_4$) | % Converted Carbon Atoms Appearing as Light Aromatics in the Product |
|---|---|---|
| 1125 | 0 | 47 |
| 1150 | 15 | 55 |
| 1150 | 20 | 53 |
| 1150 | 25 | 60 |

TABLE II

Constant Conversion of 25%, GHSV = 9000 hr$^{-1}$

| Temperature, °C. | % H$_2$ (Balance CH$_4$) | % Converted Carbon Atoms Appearing as Light Aromatics in the Product |
|---|---|---|
| 1145 | 0 | 40 |
| 1160 | 15 | 51 |
| 1160 | 20 | 52 |
| 1160 | 25 | 53 |

TABLE III

Constant Conversion of 30%, GHSV = 9000 hr$^{-1}$

| Temperature, °C. | % H$_2$ (Balance CH$_4$) | % Converted Carbon Atoms Appearing as Light Aromatics in the Product |
|---|---|---|
| 1150 | 0 | 36 |
| 1175 | 15 | 36 |
| 1170 | 20 | 43 |
| 1175 | 25 | 46 |

Addition of H$_2$ to the methane feed gas requires that the temperature of the reaction zone be raised to maintain conversion at a constant space velocity. The beneficial effect of adding hydrogen is evidenced by the increase in the fraction of converted carbon appearing as the most desirable product, the light aromatics. Thus, hydrogen addition improves the selectivity of the catalytic conversion of methane.

The catalyst used in obtaining the data in the tables was prepared as follows. A low area support was prepared by crushing Carborundum Company fused white refractory alumina bubbles, sieving the crushed material, and retaining the 8–20 mesh fraction. The 20 g of this support was added, dropwise, a solution of 2.46 g $Th(NO_3)_4.4H_2O$ dissolved in 4 ml distilled water. After mixing throughly with a spatula, the mixture was dried at 155° C. overnight in an oven, then fired at 900° C. in air to convert $Th(NO_3)_4$ to $ThO_2$. For these experiments, the inside of the alumina reactor tube was coated with copper, by exposing it to a solution of 7 g of $Cu(C_2H_3O_2)_2.H_2O$ in methanol three times, draining and drying the tube between each exposure, then reducing the adsorbed copper salt to metallic copper for reduction in hydrogen at 300° C. To assure there was no excess of copper, the reactor tube temperature was increased to 1150° C., and an argon flow maintained through the tube for 10 hours at the elevated temperature.

The above data illustrates one preferred embodiment of the invention and the increased yield of light aromatic hydrocarbons by the addition of a small but effective amount of hydrogen added to the feed gas.

What is claimed is:

1. In a continuous catalytic process for the production of higher molecular weight hydrocarbons from lower molecular weight hydrocarbons in which a lower molecular weight hydrocarbon containing gas is contacted in a reaction zone with a higher molecuilar weight hydrocarbon synthesis catalyst under $C_2+$ hydrocarbon synthesis conditions, the improvement comprising significantly increasing the production of light aromatics by 10 to 40 weight percent by adding hydrogen to said gas thereby forming a reaction gas wherein said hydrogen comprises 1 to b 25 volume percent of the reaction gas, said synthesis conditions including a temperature greater than 1000° C. and a gas hourly space velocity of greater than 3200 $hr^{-1}$.

2. The process of claim 1 wherein said reaction zone contains a stationary or fluidized bed of a catalyst containing a carbide, nitride, boride or oxide of a Group I-A, II-A, III-A, IV-B or actinide series metal.

3. The process of claim 2 wherein said temperature is in the range of 1100° to 1200° C., said space velocity is in the range of 6000 to 36,000 $hr^{-1}$ and at least 20 mole percent of said lower molecular weight hydrocarbons is converted to higher molecular weight hydrocarbons.

4. The process of claim 3 wherein said added hydrogen comprises 2 to 20 volume percent of the reaction gas.

5. The process of claim 4 wherein said catalyst contains a Group I-A metal selected from lithium, potassium or cesium.

6. The process of claim 4 wherein said catalyst contains a Group II-A metal selected from beryllium, magnesium, calcium, strontium, barium or radium.

7. The process of claim 4 wherein said catalyst contains a Group III-A metal selected from aluminum, scandium, yttrium, lanthanum and actinium.

8. The process of claim 4 wherein said catalyst contains a Group IV-B metal selected from titanium, zircoium, and hafnium.

9. The process of claim 1 wherein said catalyst contains thorium or uranium.

10. The process of claim 1 wherein said catalyst contains a boron compound.

11. The process of claim 1 wherein said catalyst contains a silicon compound.

12. The process of claim 4 wherein said higher molecular weight hydrocarbon stream is rich in ethylene or aromatics or both.

13. In a continuous catalytic process for the production of higher molecular weight hydrocarbons from lower molecular weight hydrocarbons in which a lower molecular weight hydrocarbon containing gas is contacted in a reaction zone with a higher molecular weight hydrocarbon synthesis catalyst under $C_2+$ hydrocarbon synthesis conditions, the improvement comprising significantly increasing the production of light aromatics by 10 to 40 weight percent by adding hydrogen to said gas thereby forming a reaction gas wherein said hydrogen comprises 2 to 20 volume percent of the reaction gas, said synthesis conditions including a temperature in the range of 1150° to 1175° C., a space velocity is in the range of 9000 to 18,000 $hr^{-1}$ and wherein at least 40 mole percent of said lower molecular weight hydrocarbons is converted to higher molecular weight hydrocarbons.

14. The process of claim 13 wherein said catalyst contains a Group I-A metal selected from lithium, potassium or cesium.

15. The process of claim 13 wherein said catalyst contains a Group II-A metal selected from beryllium, magnesium, calcium, strontium, barium or radium.

16. The process of claim 13 wherein said catalyst contains a Group III-A metal selected from aluminum, scandium, yttrium, lanthanum and actinium.

17. The process of claim 13 wherein said catalyst contains a Group IV-B metal selected from titanium, zirconium, and hafnium.

18. The process of claim 13 wherein said catalyst contains thorium or uranium.

19. The process of claim 13 wherein said catalyst contains a boron compound.

20. The process of claim 13 wherein said catalyst contains a silicon compound.

21. The process of claim 13 wherein said higher molecular weight hydrocarbon stream is rich in ethylene or aromatics or both.

22. In a continuous catalytic process for the production of higher molecular weight hydrocarbons from lower molecular weight hydrocarbons in which a lower molecular weight hydrocarbon containing gas is contacted in a reaction zone with a higher molecular weight hydrocarbon synthesis catalyst under $C_2+$ hydrocarbon synthesis conditions, the improvement comprising significantly increasing the production of light aromatics by 10 to 40 weight percent by adding hydrogen to said gas thereby forming a reaction gas wherein said hydrogen comprises 5 to 15 volume percent of the reaction gas, said synthesis conditions including a temperature in the range of 1150° to 1175° C., a space velocity is in the range of 9000 to 18,000 $hr^{-1}$, said catalyst contains a carbide, nitride, boride or oxide of a Group I-A, II-A, III-A, IV-B or actinide series metal and wherein at least 40 mole percent of said lower molecular weight hydrocarbons is converted to higher molecular weight hydrocarbons.

23. The process of claim 1 wherein said lower molecular weight hydrocarbon consists of methane.

24. The process of claim 13, wherein said lower molecular weight hydrocarbon consists of methane.

25. The process of claim 22 wherein said lower molecular weight hydrocarbon consists of methane.

* * * * *